(12) United States Patent
Oh

(10) Patent No.: US 8,435,245 B2
(45) Date of Patent: May 7, 2013

(54) SURGICAL IMPLANT INSERTION APPARATUS AND METHOD

(75) Inventor: YoungHoon Oh, Montville, NJ (US)

(73) Assignee: Custom Spine, Inc., Parsippany, NJ (US)

( * ) Notice: Subject to any disclaimer, the term of this patent is extended or adjusted under 35 U.S.C. 154(b) by 741 days.

(21) Appl. No.: 12/641,202

(22) Filed: Dec. 17, 2009

(65) Prior Publication Data

US 2011/0152952 A1    Jun. 23, 2011

(51) Int. Cl.
*A61B 17/88* (2006.01)
(52) U.S. Cl.
USPC ............... 606/86 A; 606/279; 606/99
(58) Field of Classification Search .......... 606/250–279, 606/86 A, 86 R, 99
See application file for complete search history.

(56) References Cited

U.S. PATENT DOCUMENTS

| | | | |
|---|---|---|---|
| 2,358,867 A | 9/1944 | Madan | |
| 3,641,332 A | 2/1972 | Reick et al. | |
| 3,774,614 A | 11/1973 | Cook | |
| 4,009,382 A | 2/1977 | Nath | |
| 4,085,436 A | 4/1978 | Weiss | |
| 4,226,228 A | 10/1980 | Shin et al. | |
| 4,562,832 A | 1/1986 | Wilder et al. | |
| 4,627,421 A | 12/1986 | Symbas et al. | |
| 5,143,436 A | 9/1992 | Baylor et al. | |
| 5,159,921 A | 11/1992 | Hoover | |
| 5,448,990 A | 9/1995 | De Faria-Correa | |
| 5,520,611 A | 5/1996 | Rao et al. | |
| 5,735,792 A | 4/1998 | Vanden Hoek et al. | |
| 5,745,632 A | 4/1998 | Dreyer | |
| 6,036,328 A | 3/2000 | Ohtsuki et al. | |
| 6,142,935 A | 11/2000 | Flom et al. | |
| 6,162,172 A | 12/2000 | Cosgrove et al. | |
| 6,176,824 B1 | 1/2001 | Davis | |
| 6,196,968 B1 | 3/2001 | Rydin et al. | |
| 6,228,025 B1 | 5/2001 | Hipps et al. | |
| 6,322,499 B1 | 11/2001 | Evans et al. | |
| 6,350,236 B1 | 2/2002 | Hipps et al. | |
| 2001/0001260 A1 | 5/2001 | Parker et al. | |

*Primary Examiner* — Eduardo C Robert
*Assistant Examiner* — Tara Carter
(74) *Attorney, Agent, or Firm* — Rahman LLC

(57) ABSTRACT

A surgical implant insertion device including an inner shaft; shaft threading coupled to the inner shaft; a rotating knob including a channel bored therethrough and internal threading lining the channel, where the internal threading configured to mate with the shaft threading; an actuator including an actuator body and a translation cavity cut through the actuator body and an inner shaft cavity cut through the actuator body, where the inner shaft cavity wraps around the inner shaft; an outer sleeve covering the inner shaft and coupled to the rotating knob; and a base connector wrapping around the outer sleeve, the base connector comprising a pair of connecting arms configured to loosely mate with the translation cavity of the actuator and pivoting and translating the actuator in response to a linear force.

19 Claims, 19 Drawing Sheets

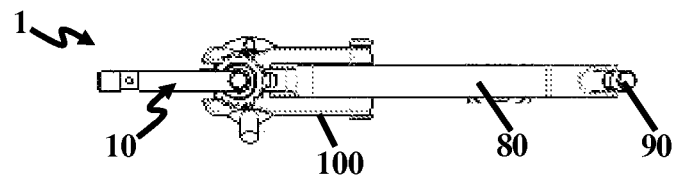
FIG. 1(B)
FIG. 1(A)
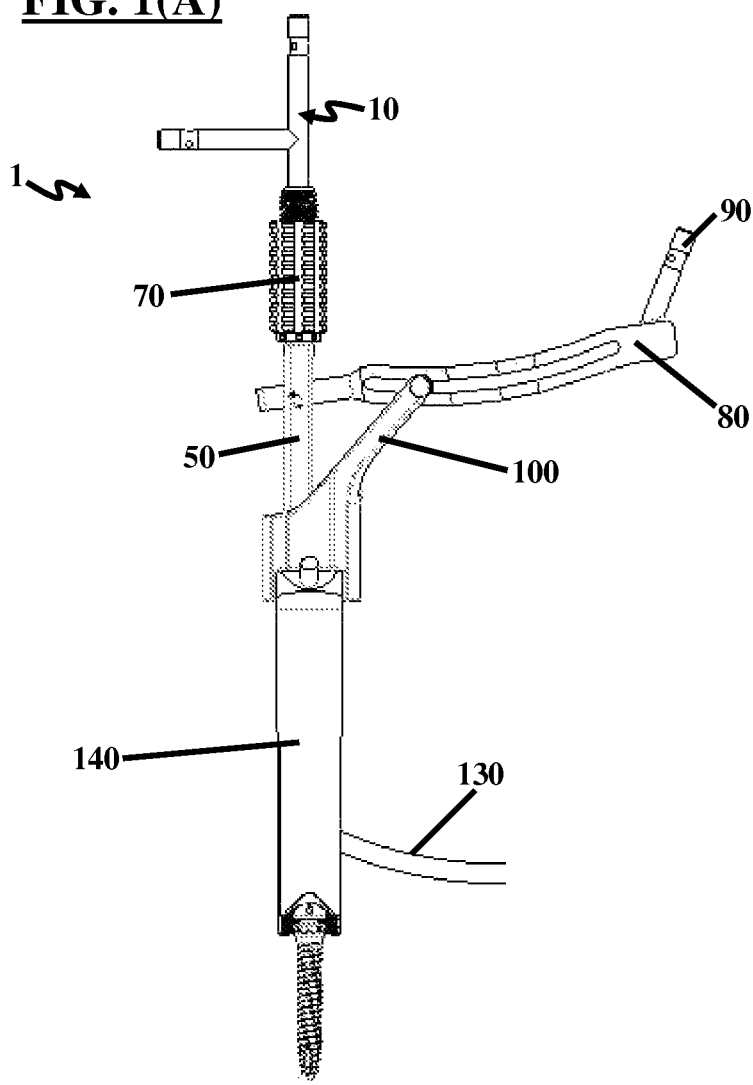

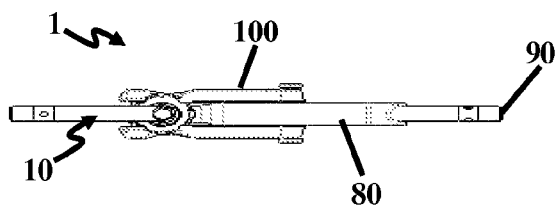
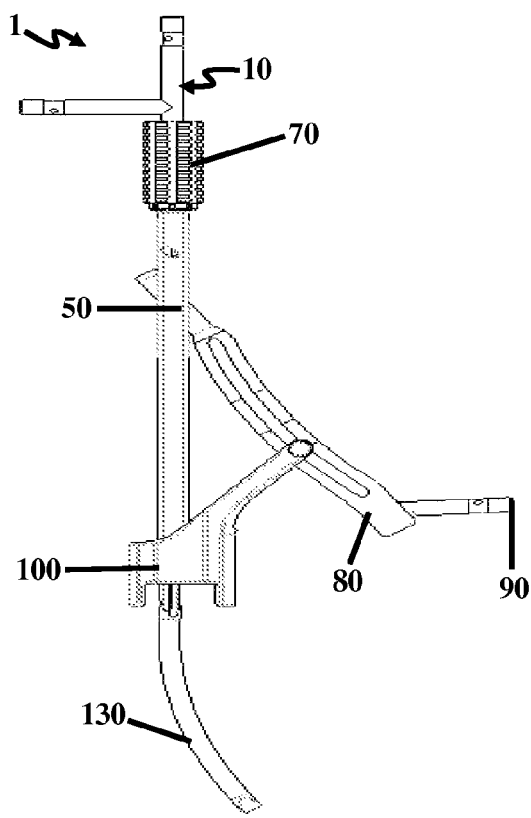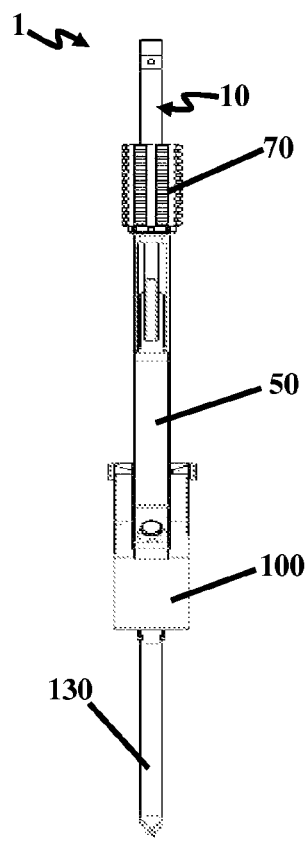

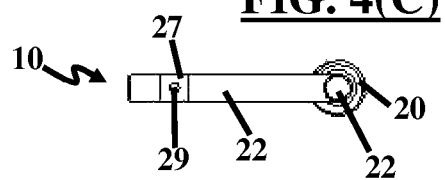
FIG. 4(C)
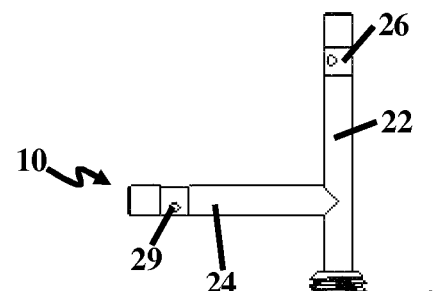
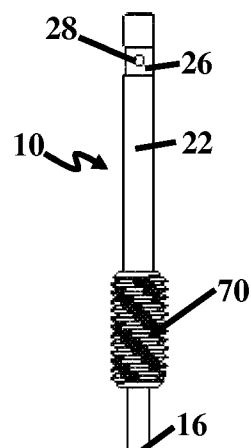
FIG. 4(A)
FIG. 4(B)
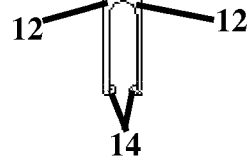

FIG. 5(C)
FIG. 5(B)
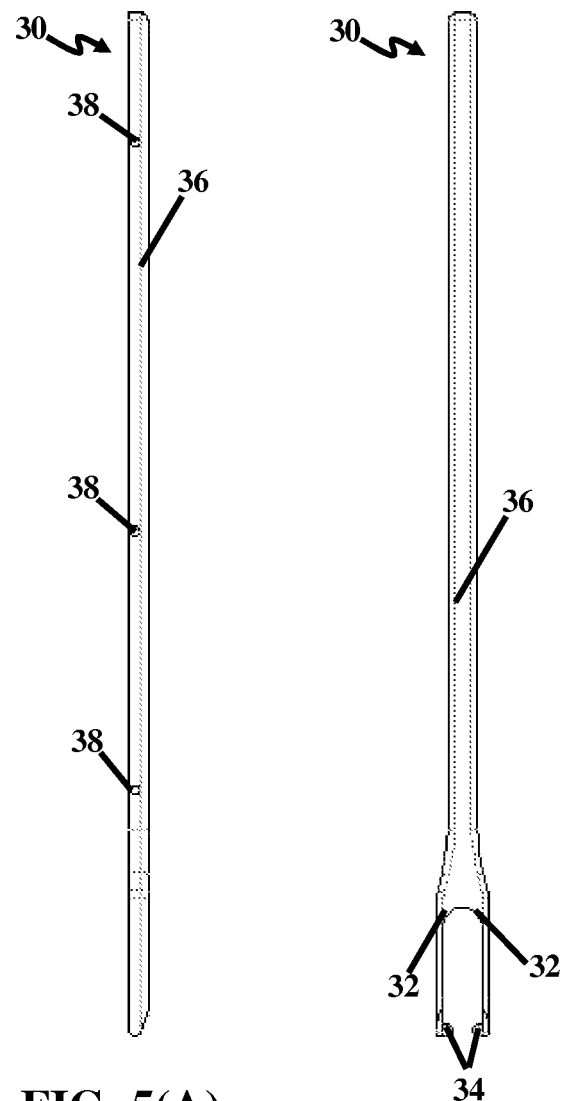
FIG. 5(A)

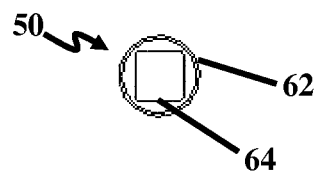
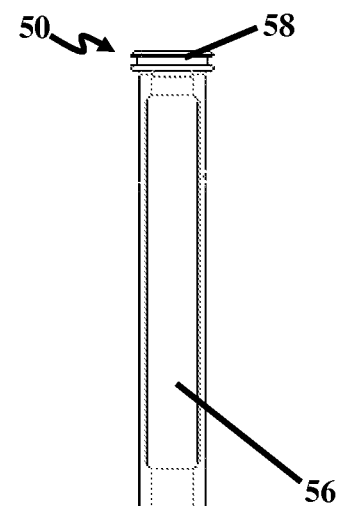
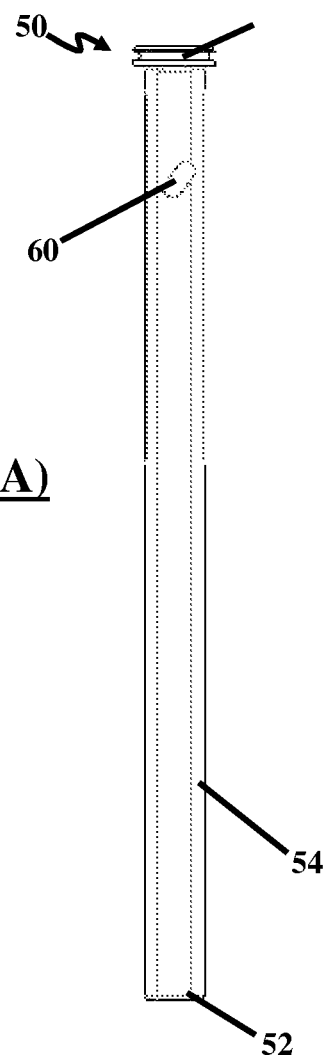

SECTION A-A

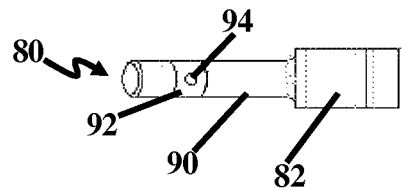
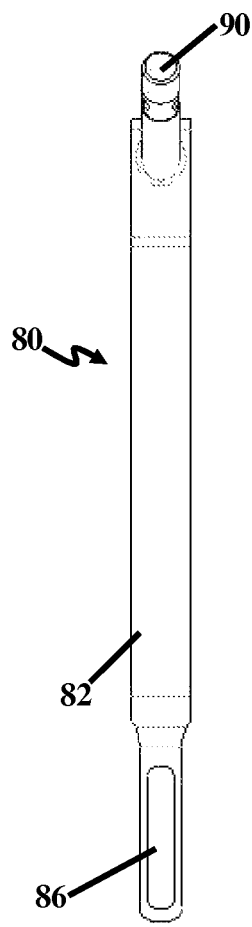
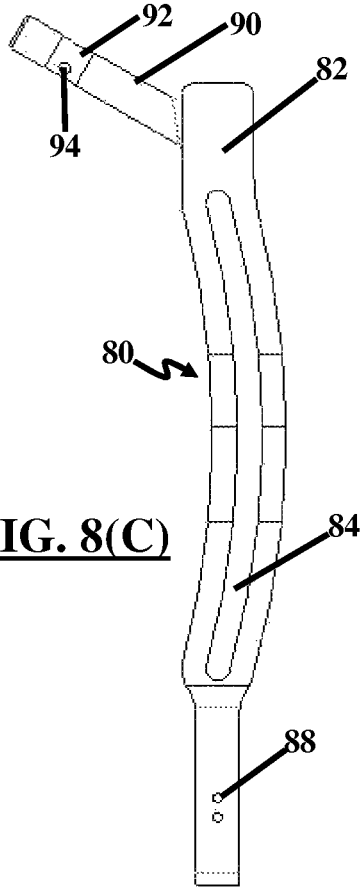
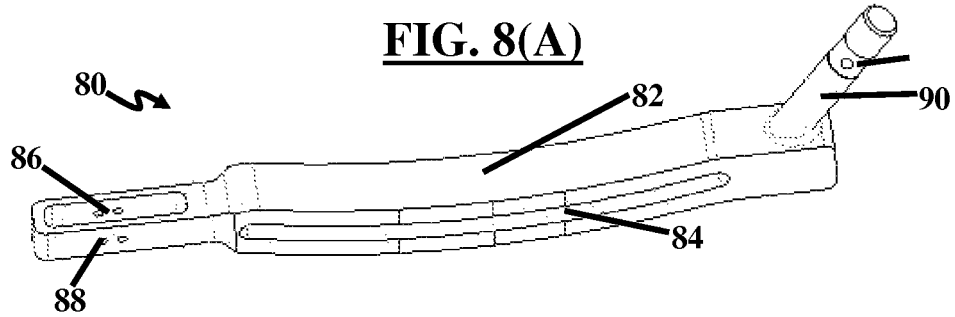

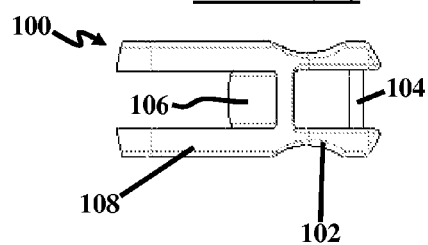
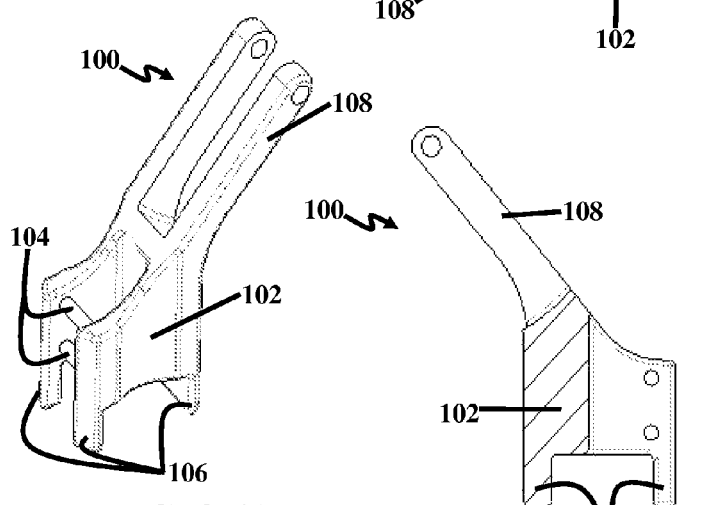
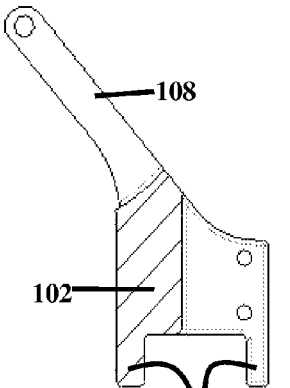
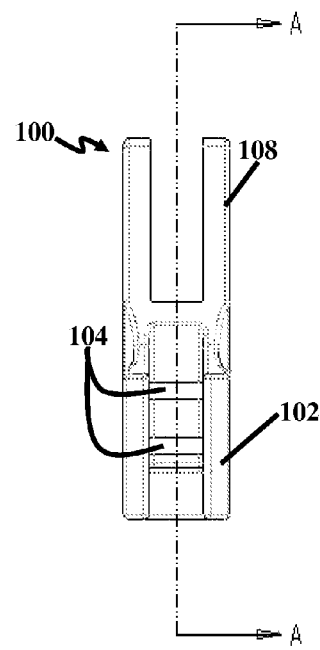
FIG. 9(D)
FIG. 9(A)
FIG. 9(B)
FIG. 9(C)

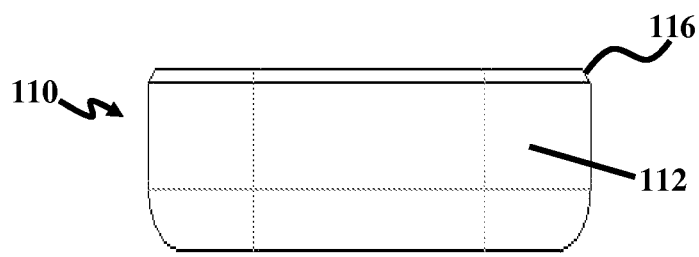
FIG. 10(C)
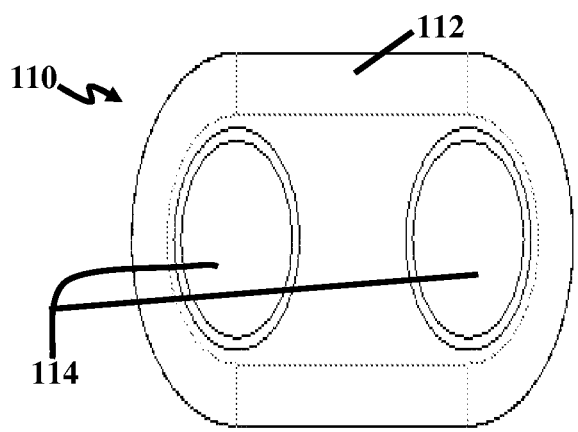 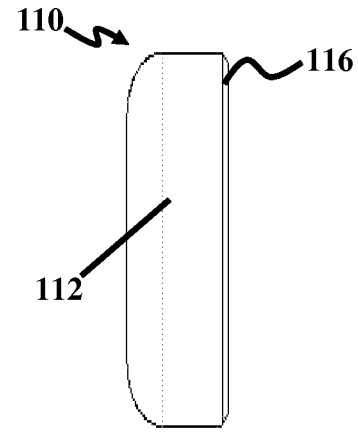
FIG. 10(A)      FIG. 10(B)

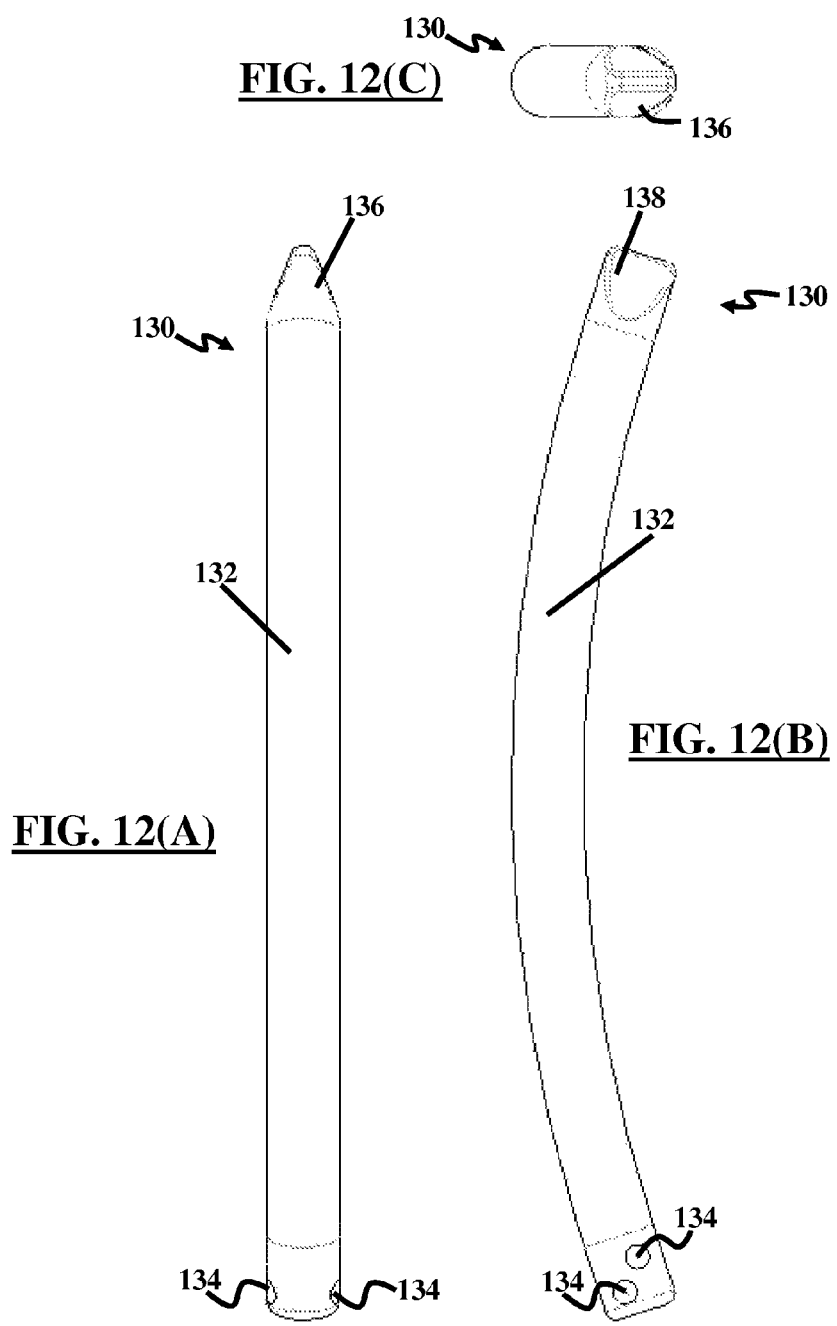

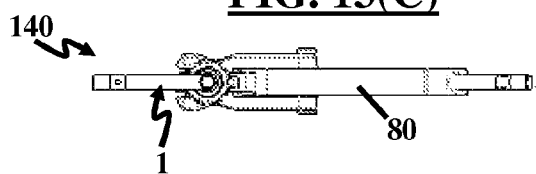
FIG. 13(C)
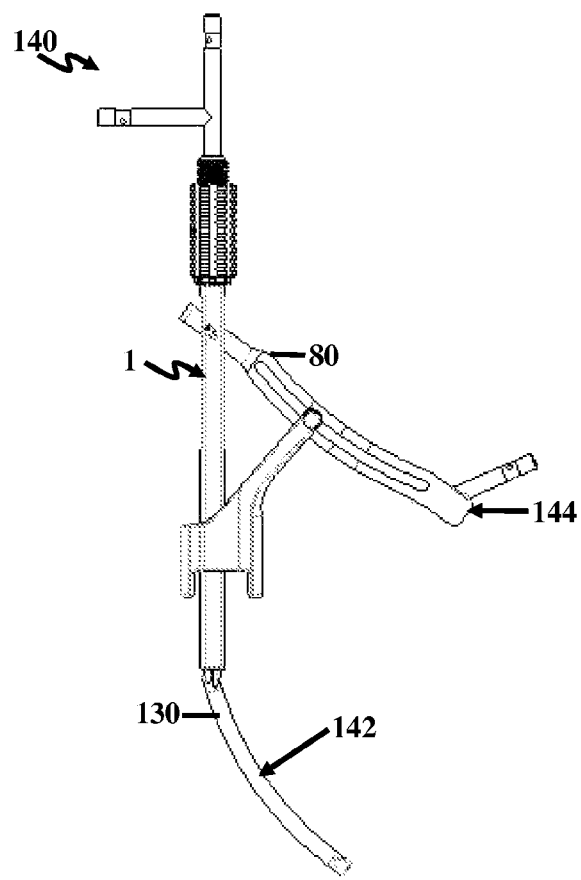 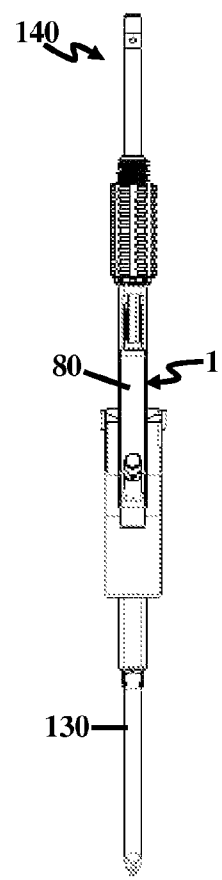
FIG. 13(A)  FIG. 13(B)

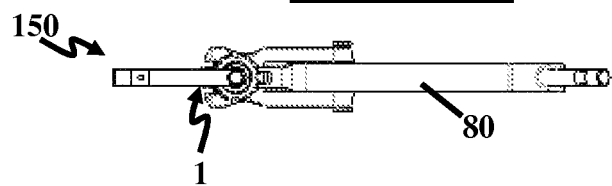
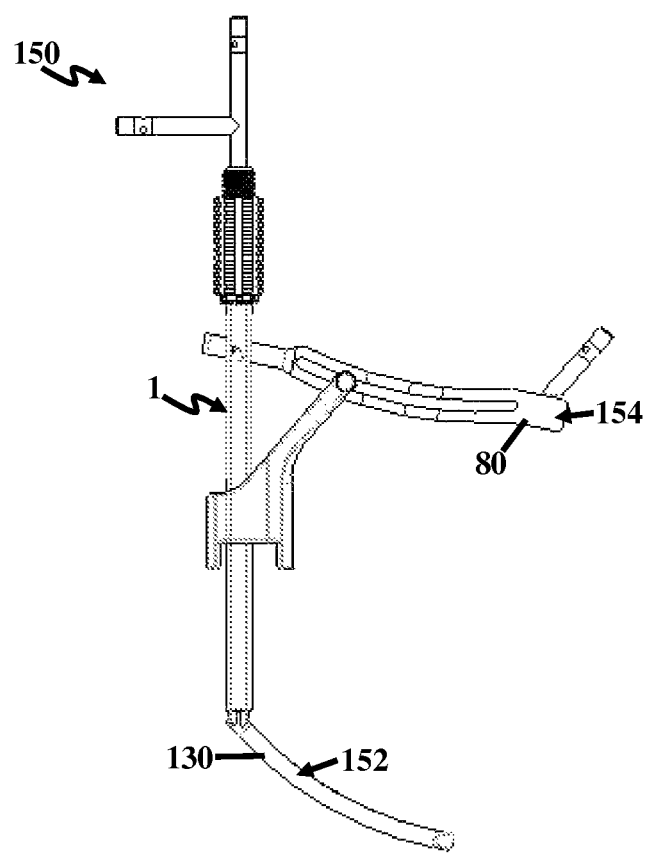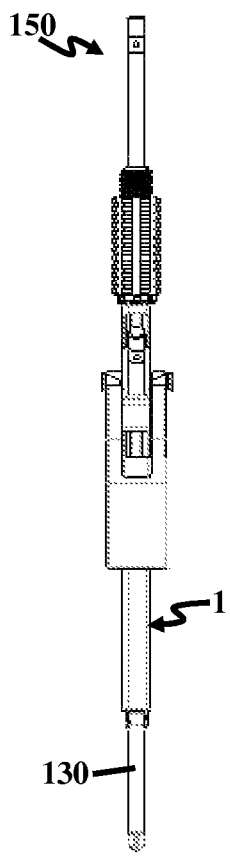
FIG. 14(C)
FIG. 14(A)     FIG. 14(B)

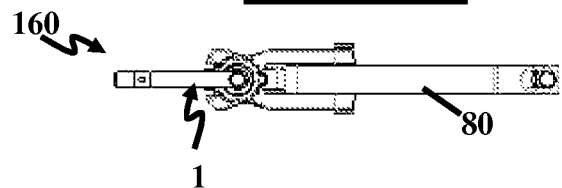
FIG. 15(C)
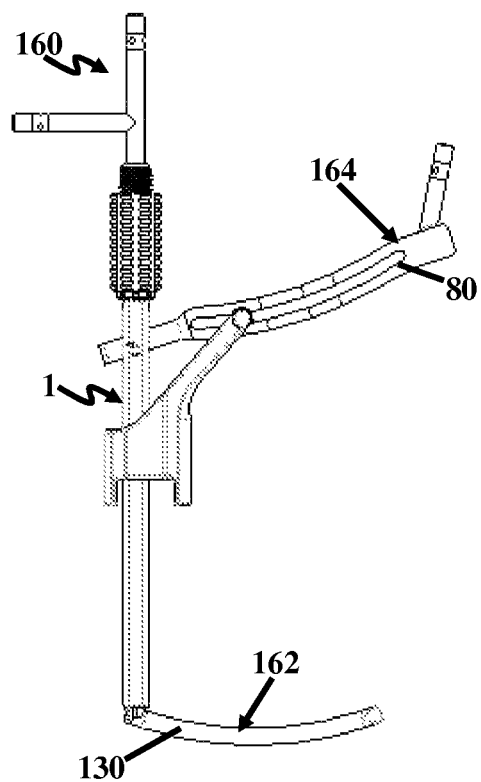
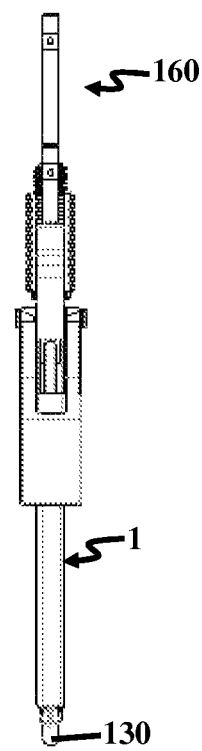
FIG. 15(A)　　　　FIG. 15(B)

FIG. 16(C)
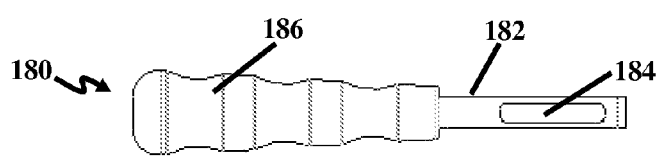
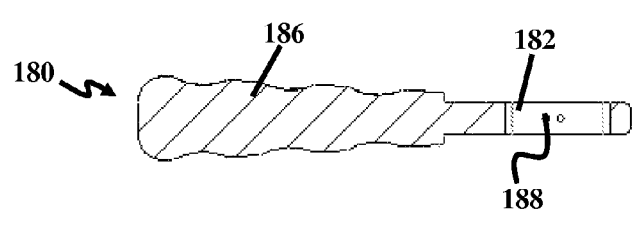
SECTION A-A
FIG. 16(B)
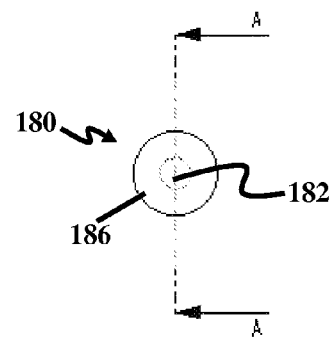
FIG. 16(A)

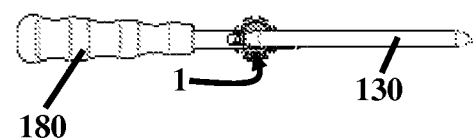
FIG. 17(C)
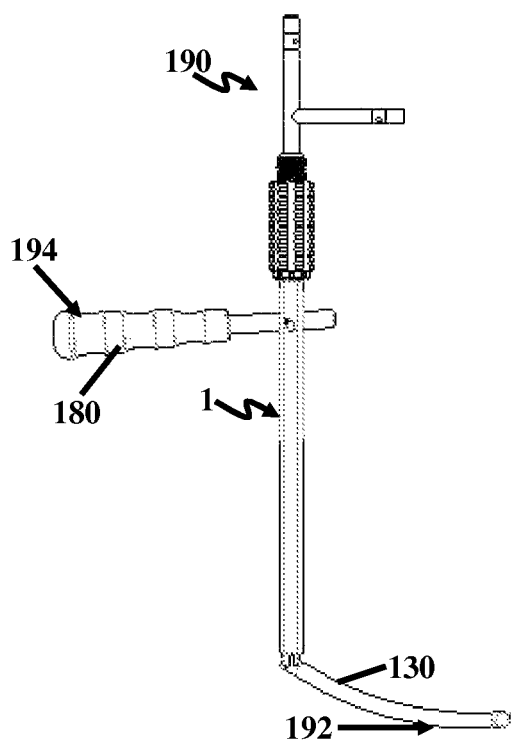 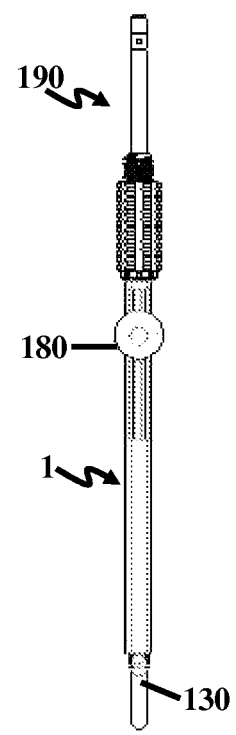
FIG. 17(A)            FIG. 17(B)

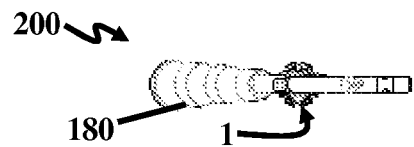
FIG. 18(C)
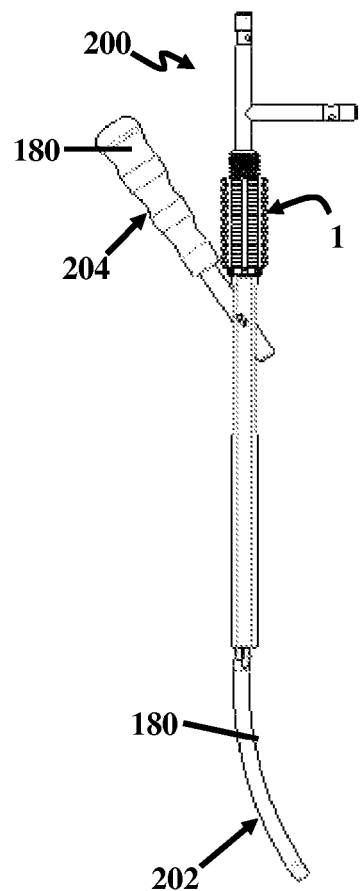
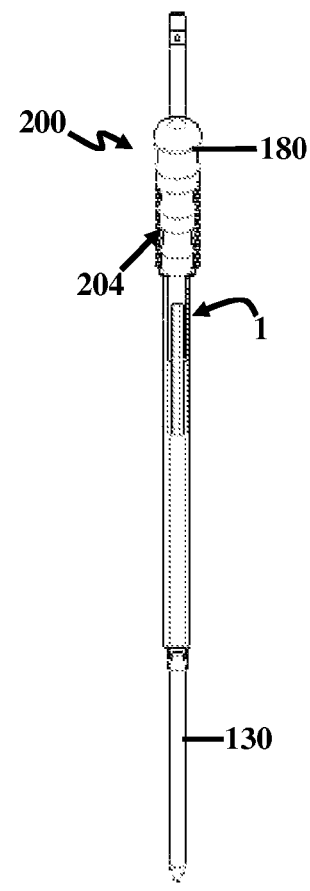
FIG. 18(A)  FIG. 18(B)

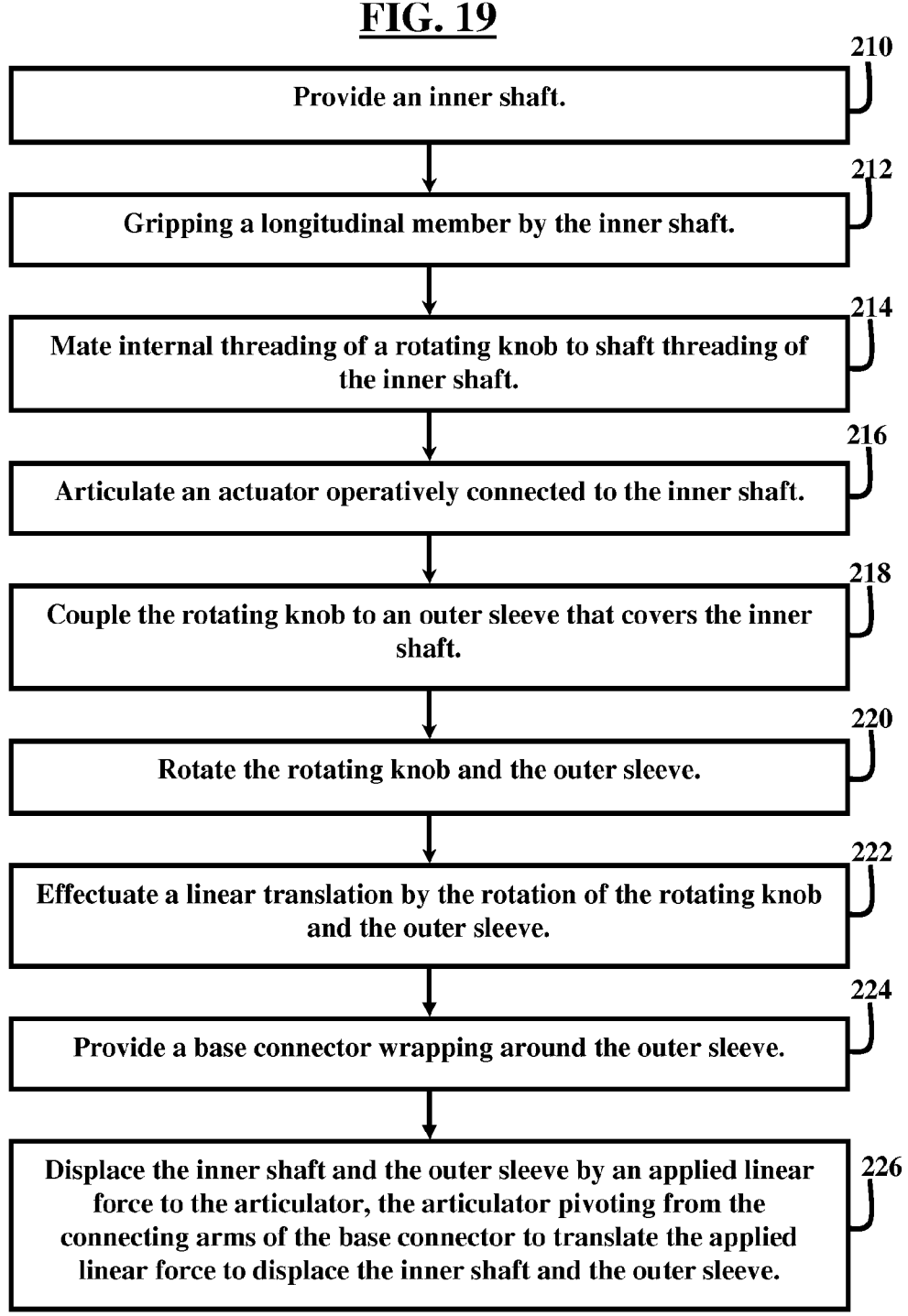

SURGICAL IMPLANT INSERTION APPARATUS AND METHOD

BACKGROUND

1. Technical Field

The embodiments described herein generally relate to medical devices, and, more particularly, to medical devices used for spinal implant surgeries.

2. Description of the Related Art

Traditional surgical procedures for pathologies located within the body have historically cause significant trauma to the intervening tissues. These procedures often require a long incision, extensive muscle stripping, prolonged retraction of tissues, denervation and devascularization of tissue. Such procedures can require operating room time of several hours and several weeks of post-operative recovery time due to the destruction of tissue during the surgical procedure. In many cases, these invasive procedures lead to permanent scarring and pain that can be more severe than the pain leading to the surgical intervention.

The development of percutaneous surgical procedures has yielded a major improvement in reducing recovery time and post-operative pain because minimal dissection of tissue, such as muscle tissue, is required. For example, minimally invasive surgical techniques are desirable for spinal and neurosurgical applications because of the need for access to locations within the body and the danger of damage to vital intervening tissues. While developments in minimally invasive surgery are steps in the right direction, there remains a need for further development in minimally invasive surgical instruments and methods. For example, conventional surgical instruments used during minimally invasive surgical procedures provide limited movement surgery and offer limited depth control during the procedure. These shortcomings to convention minimally invasive surgical instruments frequently raise the risk of additional morbidity to a patient undergoing a minimally invasive surgical procedure.

SUMMARY

In view of the foregoing, an embodiment herein provides an apparatus for inserting a rod, the apparatus comprising: an inner shaft comprising: a first inner shaft comprising: a first pair of gripping arms; and a first main body having a first length and comprising a first cross-section dimension, wherein the first main body is coupled to the first pair of gripping arms; a second inner shaft comprising: a second pair of gripping arms, wherein the first pair of gripping arms and the second pair of gripping arms together grip the rod; and a second main body having the first length and comprising a second cross-section dimension, wherein the second main body is coupled to the second pair of gripping arms and the second cross-section dimension is configured to mate with the first cross-section dimension; and a shaft threading coupled to the first main body of the first inner shaft; a rotating knob comprising a channel bored therethrough and internal threading lining the channel, the internal threading configured to mate with the shaft threading; an actuator comprising an actuator body and a translation cavity cut through the actuator body and an inner shaft cavity cut through the actuator body, wherein the inner shaft cavity wraps around the first cross-section dimension and the second cross-section dimension of the inner shaft; an outer sleeve covering the first main body and the second main body of the inner shaft and coupled to the rotating knob; and a base connector wrapping around the outer sleeve, the base connector comprising a pair of connecting arms configured to loosely mate with the translation cavity of the actuator and pivoting and translating the actuator in response to a linear force.

Such a device may further comprise a plurality of connecting hinges and pins that couple the first main body to the second main body. In addition, the inner shaft may further comprise a cylindrical body coupled to the shaft threading; and a perpendicular body coupled to the cylindrical body. Moreover, when a torque is applied to the rotating knob and outer sleeve may effectuate a linear translation in one of a first direction and a second direction. Furthermore, the linear translation in the first direction may translate the outer sleeve to extend and partially cover the first pair of gripping arms and the second pair of gripping arms and thereby compressing each gripping arm of the first pair of gripping arms and each gripping arm of the second pair of gripping arms together. Additionally, the linear translation in the second direction may translate the outer sleeve to retract from the first pair of gripping arms and the second pair of gripping arms. The linear force may also be applied in a linear direction to the actuator and may effectuate a linear translation to the inner shaft and the outer sleeve in one of a first direction and a second direction.

Such a linear translation in the first direction and the second direction may translate each of the outer sleeve and the inner shaft in an opposite direction to the linear direction. In addition, the inner shaft and the outer sleeve may respond in unison to the linear translation.

An embodiment herein further provides a system for longitudinal member insertion through a percutaneous tube, the system comprising: a longitudinal member comprising a main body and a plurality of gripping cavities; an inner shaft comprising: a first inner shaft comprising: a first pair of gripping arms; and a first main body comprising a first length and a first cross-section dimension, wherein the first main body is coupled to the first pair of gripping arms; a second inner shaft comprising: a second pair of gripping arms, wherein the second pair of gripping arms and the first pair of gripping arms together grip longitudinal member; and a second main body comprising the first length and a second cross-section dimension, wherein the second main body is coupled to the second pair of gripping arms and the second cross-section dimension is configured to mate with the first cross-section dimension; and a shaft threading coupled to the first main body of the first inner shaft; a rotating knob with a channel bored therethrough and internal threading lining the channel, the internal threading configured to mate with the shaft threading; an actuator comprising an actuator body and a translation cavity cut through the actuator body and an inner shaft cavity cut through the actuator body, wherein the inner shaft cavity is configured to mate with the inner shaft around the first cross-section dimension and the second cross-section dimension; an outer sleeve covering the first main body and the second main body of the inner shaft and coupled to the rotating knob; and a base connector wrapping around the outer sleeve, the base connector comprising a pair of connecting arms loosely mating with the translation cavity of the actuator and pivoting and translating in response to a linear force.

In such a system, the first pair of gripping arms may comprise a first pair of nubs and the second pair of gripping arms may comprise a second pair of nubs, and the first pair of nubs together with the second pair of nubs grips the longitudinal member at the plurality of gripping cavities. Such a system may further comprise a plurality of connecting hinges and pins that securely couple the first main body to the second main body. When a torque is applied to the rotating knob and outer sleeve, it may effectuate a linear translation in one of a first direction and a second direction. In addition, the linear translation in the first direction may translate the outer sleeve to extend and partially cover and pinch the first pair of gripping arms and the second pair of gripping arms together and thereby compress each gripping arm of the first pair of gripping arms and each gripping arm of the second pair of gripping arms together to lock the longitudinal member between the first pair of gripping arms and the second pair of gripping arms.

Moreover, the linear translation in the second direction may translates the outer sleeve to retract from the first pair of gripping arms and the second pair of gripping arms and thereby unlock the longitudinal member from between the first pair of gripping arms and the second pair of gripping arms. Furthermore, the linear force may be applied in a linear direction to the actuator and may effectuate a linear translation to the inner shaft and the outer sleeve in one of a first direction and a second direction. In addition, the linear translation in the first direction and the second direction may each translate the outer sleeve and the inner shaft in an opposite direction to the linear direction and thereby adjusting a depth of the longitudinal member within the percutaneous tube. Furthermore, the inner shaft may further comprise a cylindrical body coupled to the shaft threading and a perpendicular body coupled to the cylindrical body. Additionally, the outer sleeve further comprises an outer cylindrical surface and an inner polygonal surface.

An embodiment herein also provides a method of inserting a longitudinal member during minimally invasive surgery, the method comprising: providing an inner shaft comprising a first and second pair of gripping arms and a shaft threading operatively connected to the first pair of gripping arms; gripping the longitudinal member by the first and second pair of gripping arms; mating internal threading of a rotating knob to the shaft threading of the inner shaft; articulating an actuator operatively connected to the inner shaft; coupling the rotating knob to an outer sleeve that covers the inner shaft; rotating the rotating knob and the outer sleeve; effectuating a linear translation by the rotation of the rotating knob and the outer sleeve, the linear translation of the outer sleeve effectuating at least one of a compression of the first pair of gripping arms and the second pair of gripping arms together to lock the longitudinal member and an uncompression of the first pair of gripping arms and the second pair of gripping arms together to unlock the longitudinal member; providing a base connector wrapping around the outer sleeve, the base connector comprising a pair of connecting arms configured to loosely mate with the translation cavity of the actuator; and displacing the inner shaft and the outer sleeve by an applied linear force to the actuator, the actuator pivoting from the connecting arms of the base connector to translate the applied linear force to displace the inner shaft and the outer sleeve.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiments herein will be better understood from the following detailed description with reference to the drawings, in which:

FIGS. 1(A) and 1(B) illustrate a schematic diagram of an adjustable rod inserter in a percutaneous tube according to an embodiment herein;

FIGS. 2(A) through 2(C) illustrate a schematic diagram of an adjustable rod inserter with an unsecured longitudinal member according to an embodiment herein;

FIGS. 4(A) through 4(C) illustrate a schematic diagram of a left inner shaft of the adjustable rod inserter according to an embodiment herein;

FIGS. 5(A) through 5(C) illustrate a schematic diagram of a right inner shaft of the adjustable rod inserter according to an embodiment herein;

FIGS. 6(A) through 6(C) illustrate a schematic diagram of an outer sleeve of the adjustable rod inserter according to an embodiment herein;

FIGS. 8(A) through 8(D) illustrate a schematic diagram of an actuator of the adjustable rod inserter according to an embodiment herein;

FIGS. 9(A) through 9(D) illustrate a schematic diagram of a base connector of the adjustable rod inserter according to an embodiment herein;

FIGS. 10(A) through 10(C) illustrate schematic diagram of a hinge of the adjustable rod inserter according to an embodiment herein;

FIGS. 12(A) through 12(C) illustrate a schematic diagram of a longitudinal member of the adjustable rod inserter according to an embodiment herein;

FIGS. 13(A) through 15(C) illustrate a schematic diagram of an adjustable rod inserter in alternate positions during articulation of a rod according to an embodiment herein;

FIGS. 16(A) through 16(C) illustrate a schematic diagram of another actuator of the adjustable rod inserter according to an embodiment herein;

FIGS. 17(A) through 18(C) illustrate a schematic diagram of an adjustable rod inserter in alternate positions during articulation of a rod according to an embodiment herein; and FIG. 19 is a flow diagram illustrating a preferred method according to an embodiment herein.

DETAILED DESCRIPTION OF PREFERRED EMBODIMENTS

Figure 3C:
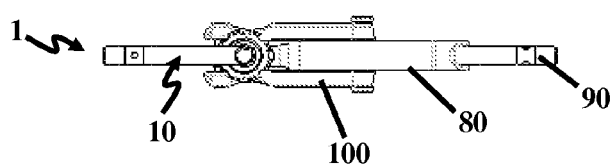
FIGS. 3(A) through 3(C) illustrate a schematic diagram of an adjustable rod inserter with a secured longitudinal member according to an embodiment herein.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

As mentioned above, there remains a need for a novel implant insertion device and method for use during minimally invasive surgical procedures (e.g., spinal surgeries that utilize a small incision) that allows greater manipulation of the surgical instrument (e.g. during placement of a surgical implant, such as a spinal rod) during surgery and allows greater depth control. The embodiments herein provide an adjustable rod inserter that may function as a traditional rod inserter or as a minimal access/invasive rod inserter for spinal surgery, and more specifically a rod inserter that holds and locks a rod in a vertical or semi-vertical position from one end and allows the rod to be inserted at any depth and allows the depth to be adjusted within an incision. Referring now to the drawings, and more particularly to FIGS. 1(A) through 19, there are shown preferred embodiments.

FIGS. 1(A) and 1(B), with reference to FIGS. 5(A) through 5(C) and 7(A) through 8(D), illustrate a schematic diagram of an adjustable rod inserter 1 in a percutaneous tube 140 according to an embodiment herein. Adjustable rod inserter 1 generally includes a left inner shaft 10 and a right inner shaft 30 (shown in FIGS. 5(A) through 5(C)). Together, left inner shaft 10 and right inner shaft 30 are partially covered by an outer sleeve 50. In addition, a rotating knob 70 is loosely coupled to left inner shaft 10. An actuator 80 is coupled to both a base connector 100 and inner shaft 10, 30. While not shown in FIGS. 1(A) and 1(B), left inner shaft 10 and right inner shaft 30 are securely coupled to each other by a plurality of connecting hinges 110 (shown in FIGS. 7(A) through 7(C)) and a plurality of pins 120 (shown in FIGS. 8(A) through 8(C)). Through the coupling of left inner shaft 10 to right inner shaft 30 by connection hinges 110 and pins 120, inner shaft 10, 30 moves uniformly and in unison. FIG. 1(A) also shows a longitudinal member 130 and a percutaneous tube 140, which may be used with the inserter 1. Longitudinal member 130 may include a spinal rod, as shown in FIG. 1(A); however, longitudinal member 130 is not limited to a spinal rod and may include any surgical implant.

FIGS. 2(A) through 2(C), with reference to FIGS. 1(A) through 1(C), illustrate a schematic diagram of an adjustable rod inserter 1 with an unsecured longitudinal member 30 according to an embodiment herein. As shown, left gripping arms 12 of left inner shaft 10 and right gripping arms 32 of right inner shaft 30 together grip longitudinal member 130. As described in more detail below, gripping arms 12, 32 may be forked-shaped, so that each will bend outward when gripping longitudinal member 130. In the configuration shown in FIGS. 2(A) through 2(C), longitudinal member 130 is not locked within gripping arms 12, 32 and easy removal of longitudinal member 130 from gripping arm 12, 32 is possible. In addition, outer sleeve 50 is shown in FIGS. 3(A) and 3(B) in a retracted position. In the retracted position, outer sleeve 50 is not in contact with gripping arms 12, 32. As discussed in further detail below, retraction of outer sleeve 50 is controlled by rotating knob 70.

Figure 3A:
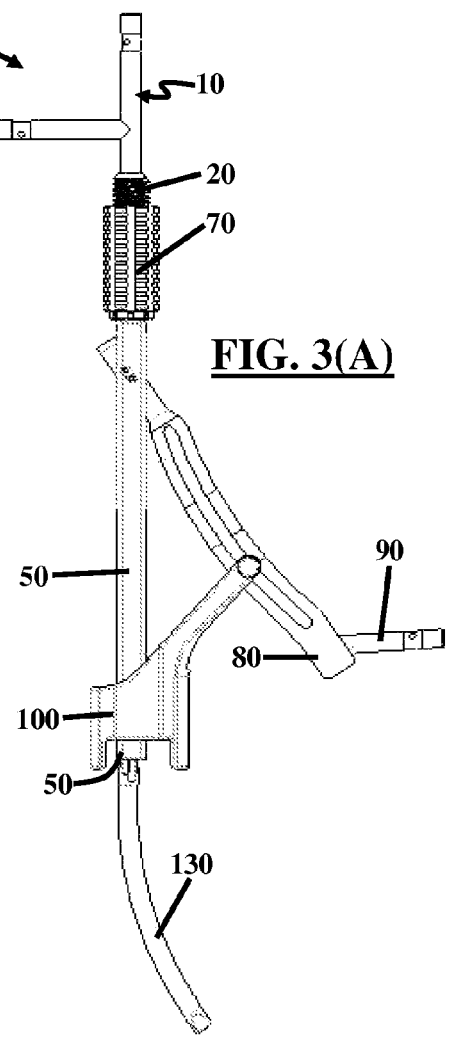
Figure 3B:
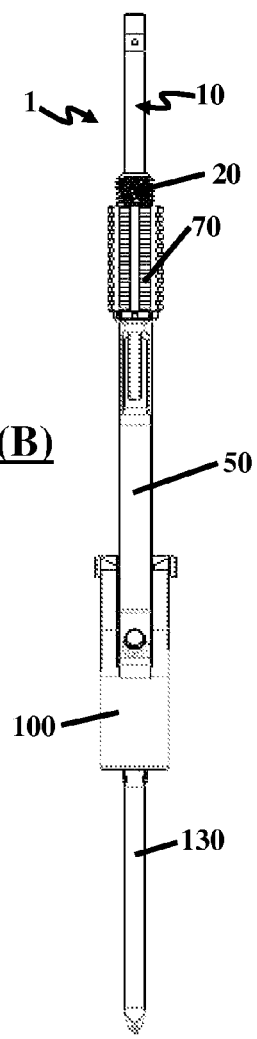

FIGS. 3(A) through 3(C), with reference to FIGS. 1(A) through 2(C), illustrate a schematic diagram of an adjustable rod inserter 1 with a secured longitudinal member 130 according to an embodiment herein. Similar to FIGS. 2(A) through 2(C), gripping arms 12, 32 together grip longitudinal member 130. In FIGS. 3(A) through 3(C), however, longitudinal member 130 is locked and securely gripped by gripping arms 12, 32 to prevent easy removal of longitudinal member 130. As shown in FIG. 3(A), outer sleeve 50 is in an extended position. In the extended position, outer sleeve 50 is in contact with gripping arms 12, 32 to thereby compress (or pinch) gripping arms 12, 32 together and lock longitudinal member 130. As discussed in further detail below, extension of outer sleeve 50 is controlled by rotating knob 70.

FIGS. 4(A) through 4(C), with reference to FIGS. 1(A) through 3(C), 5(B) and 12(A) through 12(C), illustrate a schematic diagram of a left inner shaft of the adjustable rod inserter, according to an embodiment herein. As shown, left inner shaft 10 includes a pair of gripping arms 12, a pair of gripping nubs 14, a flat body 16, a plurality of pinholes 18, shaft threading 20 and a cylindrical body 22. In FIG. 4(B), gripping arms 12 are shown to be forked-shaped; however, other configurations are possible. The configuration of gripping arms 12 shown in FIG. 4(B) provides gripping arms 12 with some flex, so that each gripping arm 12 may bend slightly outwards to accommodate a longitudinal member 130 between gripping arms 12. The slight flex of gripping arms 12 also allows outer sleeve 50 to slide over gripping arms 12 and by so doing, compress (or pinch) gripping arms 12 together. When longitudinal member 130 is between the compressed gripping arms 12, longitudinal member 130 is effectively locked between gripping arms 12. In addition, as discussed in further detail below, longitudinal member 130 includes connecting cavities 138 (shown in FIGS. 12(A) through 12(C)) configured to be mated with gripping nubs 14 (as well as gripping nubs 34, shown in FIG. 5(B)).

As shown in FIG. 4(A), flat body 16 has a roughly rectangular shape, although other configurations are possible. Flat body 16 is the approximately the same size and shape as right inner shaft 30, shown in FIGS. 5(A) through 5(C) to allow flat body 16 and right inner shaft 30 to be joined by a plurality of connecting hinges 110. A plurality of pinholes 18 are bored into flat body 16 and slightly recessed to accommodate connecting hinges 110. As shown in FIGS. 4(A) and 4(B), one end of flat body 16 is securely coupled to shaft threading 20. Shaft threading 20 is configured to mate with rotating knob 70. In addition to being coupled to flat body 16, shaft threading is also coupled to cylindrical body 22. Cylindrical body 22 may be configured to engage a corresponding handle of a handle-like device (not shown). The cylindrical body 22 comprises a recessed collar 26 and hole 28 that may lock into a corresponding pin (not shown) of the handle-like device (not shown). The shaft 10 may further comprise a perpendicular body 24 configured transverse to the cylindrical body 22, wherein the perpendicular body 24 is also configured to engage another corresponding handle of a handle-like device (not shown). The perpendicular body 24 comprises a recessed collar 27 and hole 29 that may lock into a corresponding pin (not shown) of a handle-like device (not shown).

FIGS. 5(A) through 5(C), with reference to FIGS. 1(A) through 4(C) and 12(A) through 12(C), illustrate a schematic diagram of a right inner shaft of the adjustable rod inserter 1 according to an embodiment herein. As shown, right inner shaft 30 includes a pair of gripping arms 32, a pair of gripping nubs 34, a flat body 36 and a plurality of pinholes 38. In FIG. 5(B), gripping arms 32 are shown to be forked-shaped; however, other configurations are possible. The configuration of gripping arms 32 shown in FIG. 5(B) provides gripping arms 32 with some flex, so that each gripping arm 32 may bend slightly outwards to accommodate a longitudinal member 130 between gripping arms 32. The slight flex of gripping arms 32 also allows outer sleeve 50 to slide over gripping arms 32, and by so doing, compress (or pinch) gripping arms 32 together. When longitudinal member 130 is between the compressed gripping arms 32, longitudinal member 130 is effectively locked between gripping arms 32. In addition, as discussed in further detail below, longitudinal member 130 includes connecting cavities 138 (shown in FIGS. 12(A) through 12(C)) configured to be mated with gripping nubs 34 (as well as gripping nubs 14, shown in FIG. 4(B)).

Also shown in FIG. 5(C), flat body 36 has a roughly rectangular shaped configuration, although other configurations are possible. Flat body 36 is approximately the same size and shape as flat body 16 of left inner shaft 10, shown in FIGS.

4(A) through 4(C) to allow flat body 36 and flat body 16 to be joined by a plurality of connecting hinges 110. In addition, a plurality of pinholes 18 are bored into flat body 36 and slightly recessed to accommodate connecting hinges 110.

FIGS. 6(A) through 6(C), with reference to FIGS. 1(A) through 5(C) illustrate a schematic diagram of an outer sleeve 50 of the adjustable rod inserter 1 according to an embodiment herein. As shown, outer sleeve 50 includes a distal end 52, a main body 54, an actuator cavity 56, a proximal end 58, access hole 60, a circular outer surface 62, and a polygonal inner surface 64.

Distal end 52, as shown in FIG. 6(A), is the portion of outer sleeve 50 that covers gripping arms 12, 32 to compress gripping arms 12, 32 together and lock longitudinal member 130 between the compressed gripping arms 12, 32. Main body 54 is generally smooth and cylindrical in shape. Actuator cavity 56 is cut into main body 54 to accommodate the articulated movement of actuator 80. As described in further detail below, proximal end 58 attaches to rotating knob 70 to allow lateral translation of outer sleeve 50 with respect to inner shaft 10, 30. Access hole 60 is provided to ease the assembly of adjustable rod inserter 1.

In addition, FIG. 6(C) shows outer sleeve having an outer circular surface 62, and an inner polygonal surface 64. Outer circular surface 62 is so configured to allow easy lateral movement within percutaneous tube 140 (shown in FIG. 1(A)). Inner polygonal surface 64 is so configured to accommodate the rectangular cross-section of inner shaft 10, 30 and to prevent rotational movement of inner shaft 10 with respect to outer sleeve 50.

Figure 7C:
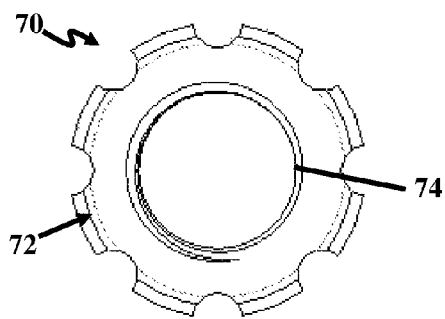
FIGS. 7(A) through 7(C) illustrate a schematic diagram of a rotating knob of the adjustable rod inserter according to an embodiment herein.
Figure 7A:
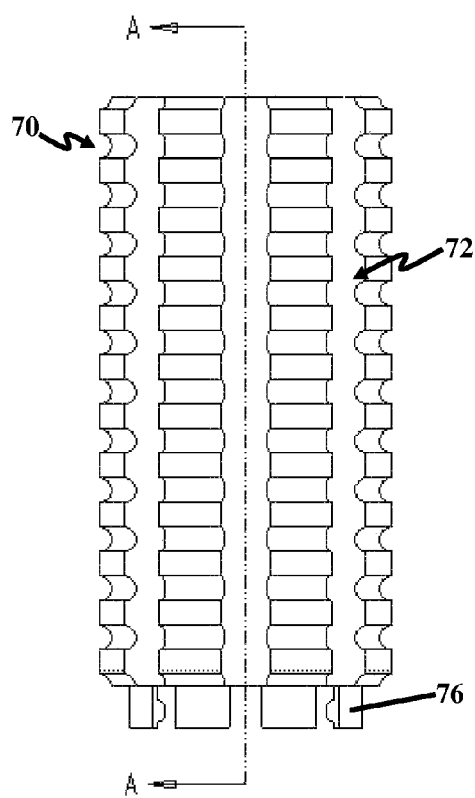
Figure 7B:
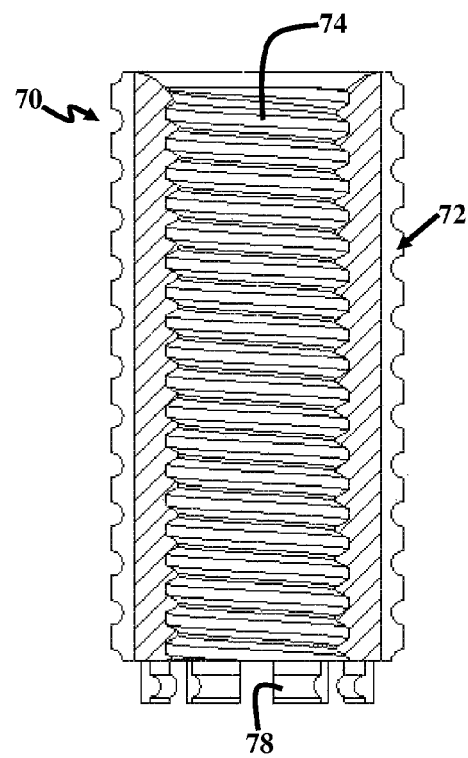

FIGS. 7(A) through 7(C), with reference to FIGS. 1(A) through 6(C), illustrate a schematic diagram of a rotating knob 70 of the adjustable rod inserter 1 according to an embodiment herein. As shown, FIG. 7(B) is a cross-section taken along the A-A axis shown in FIG. 7(A). As shown in the various views, rotating knob 70 includes a textured exterior 72, a threaded interior 74, a connecting lip 76, and a connecting groove 78. Although rotating knob 70 is shown in FIGS. 7(A) and 7(B) as roughly cylindrically shaped, it is not limited to such a configuration. In addition, while textured exterior 72 is shown in FIG. 7(A) as a pattern of deep longitudinal grooves intersecting shallow lateral grooves, textured exterior 72 is not limited to the texture shown in FIG. 7(A). Rotating knob 70 also includes threaded interior 74, wherein the threads etched therein are configured to mate with complementary threads embedded on shaft threading 20, shown in FIGS. 4(A) and 4(B). In addition, outer sleeve 50 is configured to couple to rotating knob 70 by securely clipping onto connecting lip 76 and is held in place by connecting groove 78. When outer sleeve 50 is coupled to rotating knob 70, both outer sleeve 50 and rotating knob 70 move in unison. Consequently, when rotating knob 70 is mated with shaft threading 20 and a torque is applied to rotating knob 70, both rotating knob 70 and outer sleeve 50 are subjected to a linear translation as the threading of threaded interior 74 moves along the threading of shaft threading 20.

FIGS. 8(A) through 8(D), with reference to FIGS. 1(A) through 7(C), illustrate a schematic diagram of an actuator 80 of the adjustable rod inserter 1 according to an embodiment herein. Actuator 80 provides depth control when inserting longitudinal member 130 during a minimally invasive surgical procedure. As shown in the various views of FIGS. 8(A) through 8(D), actuator 80 includes main body 82, translation cavity 84, inner shaft cavity 86, pinholes 88, control arm 90, control arm collar 92 and collar pinhole 94. As shown in FIG. 1(A), actuator 80 is coupled to base connector 100 by translation cavity 82. Additionally, actuator 80 is coupled to inner shaft 10, 30 by shaft cavity 86 and secured to inner shaft 10, 30 by pins inserted through pinholes 88. Although not shown in FIGS. 8(A) through 8(D), control arm 90 provides leverage to allow sensitive depth adjustment and greater depth control while inserting longitudinal member 130 during a minimally invasive surgical procedure. The control arm 90 comprises a recessed collar 92 and hole 94 that may lock into a corresponding pin (not shown) of a handle-like device (not shown).

FIGS. 9(A) through 9(D), with reference to FIGS. 1(A) through 8(D), illustrate a schematic diagram of a base connector 100 of the adjustable rod inserter 1 according to an embodiment herein. FIG. 9(B) is shown as a cross-section view cut along the A-A axis of FIG. 9(C). As shown, base connector 100 includes a main body 102, a plurality of support rails 104, a plurality of support legs 106 and a pair of connecting arms 108. As shown in FIG. 1(A), outer sleeve 50 is inserted through main body 102 and held in place by support rails 104. In addition, base connector 100 is anchored to percutaneous tube 140 in FIG. 1(A) by support legs 106 and coupled to actuator 80 (via translation cavity 82, shown in FIGS. 8(A) through 8(C)) by connecting arms 108.

FIGS. 10(A) through 10(C), with reference to FIGS. 1(A) through 9(D), illustrate schematic diagram of a connecting hinge 110 of the adjustable rod inserter 1 according to an embodiment herein. Connecting hinge 110 includes a main body 112, a plurality of pinholes 114. In addition, connecting hinge 110 may further include a chamfered edge 126. FIG. 10(A) shows main body 112 with two pinholes 114 bored therethrough, and each pinhole 114 is dimensioned to securely mate with a pin 120. As discussed previously, connecting hinge 110 securely couples left inner shaft 10 to right inner shaft 30 by aligning pinholes 114 with pinholes 18, 38 and securing a pin 120 through the aligned pinholes. Furthermore, pinholes 18, 38 are sufficiently recessed into inner shaft 10, 30 to permit connecting hinge 110 to sit flush with the outer surface of inner shaft 10, 30 and allow linear translation of inner shaft 10, 30 within outer sleeve 50.

Figure 11B:
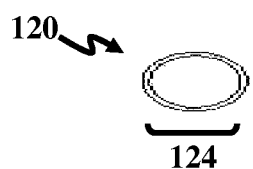
FIGS. 11(A) through 11(B) illustrate a schematic diagram of a pin of the adjustable rod inserter according to an embodiment herein.
Figure 11A:
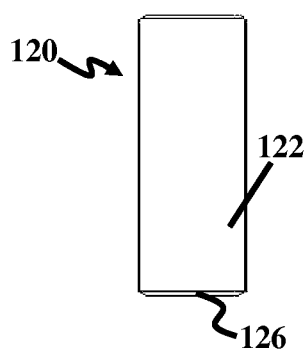

FIGS. 11(A) through 11(B), with reference to FIGS. 1(A) through 10(C), illustrate a schematic diagram of a pin 120 of the adjustable rod inserter 1 according to an embodiment herein. As shown, pin 120 includes a main body 122, which has a diameter 124. In addition, pin 120 may further include chamfered edges 126. Furthermore, diameter 124 is sufficient to securely mate with pinholes 18, 38 and pinholes 114.

FIGS. 12(A) through 12(C), with reference to FIGS. 1(A) through 11(B), illustrate a schematic diagram of a longitudinal member 130, which may be used with the adjustable rod inserter 1 according to an embodiment herein. For example, longitudinal member 130 may include a spinal rod used during spinal surgery. As shown, longitudinal member 130 includes a main body 132 with a plurality of gripping cavities 134 cut therein. In addition, longitudinal member 130 may include an elongated member 136 and a connecting cavity 138. A plurality of gripping cavities 134 are configured to mate with nubs 14, 34 on gripping arms 12, 32 and allow manipulation of longitudinal member 130, as discussed in further detail below. In addition, a first longitudinal member 130 may include elongated member 136 at a first end, wherein elongated member 136 is configured to mate with connecting cavity 136 on a second end of a second longitudinal member 130 to thereby chain more that one longitudinal member 130 together.

FIGS. 13(A) through 15(C), with reference to FIGS. 1(A) through 12(C), illustrate a schematic diagram of an adjustable rod inserter 140 in alternate positions during articulation of a rod, according to an embodiment herein. As shown in FIGS. 13(A) through 15(C), base connector 100 operates as a fulcrum from which actuator 80 pivots as actuator 80 raises and lowers outer sleeve 50 and inner shafts 10, 30 together.

In FIGS. 13(A) through 13(C), various views of adjustable rod inserter 1 in a first adjustable rod inserter position 140 are shown, wherein longitudinal member 130 is in a first longitudinal member position 142 and actuator 80 is in a first actuator position 144. In FIGS. 14(A) through 14(C), various views of adjustable rod inserter 1 in a second adjustable rod inserter position 150 are shown, wherein longitudinal member 130 is in a second longitudinal position 152 and actuator 80 is in a second actuator position 154. Second adjustable rod inserter position 150 shown in FIGS. 14(A) through 14(C) allows manipulation of longitudinal member 130 at a greater depth than first adjustable rod inserter position 140 shown in FIGS. 13(A) through 13(C). In particular, by moving actuator 80 from first actuator position 144 shown in FIG. 13(A) to second actuator position 154, shown in FIG. 14(A), longitudinal member 130 is also moved from first longitudinal member position 142 shown in FIG. 13(A) to second longitudinal member position 152 shown in FIG. 14(A).

In FIGS. 15(A) through 15(C), various views of adjustable rod inserter 1 in a third adjustable rod inserter position 160 are shown, wherein longitudinal member 130 is in a third longitudinal member position 162 and actuator 80 is in a third actuator position 164. Third adjustable rod inserter position 160 shown in FIGS. 15(A) through 15(C) allows manipulation of longitudinal member 130 at an even greater depth than first adjustable rod inserter position 140 (shown in FIGS. 13(A) through 13(C)) or second adjustable rod inserter position 150 (shown in FIGS. 15(A) through 15(C)). In particular, by moving actuator 80 from second actuator position 154 shown in FIG. 14(A) to second actuator position 164, shown in FIG. 15(A), longitudinal member 130 is also moved from second longitudinal member position 152 shown in FIG. 14(A) to third longitudinal member position 162 shown in FIG. 15(A).

FIGS. 16(A) through 16(C), with reference to FIGS. 1(A) through 15(C), 17(A), and 18(A), illustrate a schematic diagram of actuator 180 of the adjustable rod inserter 1 according to an embodiment herein. FIG. 16(B) is a cross-section of FIG. 16(A), cut along the A-A axis shown in FIG. 16(A). Similar to actuator 80, actuator 180 provides depth control when inserting longitudinal member 130 during a minimally invasive surgical procedure. As shown in the various views of FIGS. 16(A) through 16(C), actuator 180 includes main body 182, shaft cavity 184, control handle 186 and pinholes 188. As shown in FIGS. 17(A) and 18(A), actuator 180 is coupled to inner shaft 10, 30 by shaft cavity 182 and secured to inner shaft 10, 30 by pins inserted through pinholes 188. Control handle 186 provides leverage to allow sensitive depth adjustment and greater depth control while inserting longitudinal member 130 during a minimally invasive surgical procedure. The control handle 186 is configured to provide additional control and comfort during surgery.

FIGS. 17(A) through 18(C), with reference to FIGS. 1(A) through 16(C), illustrate a schematic diagram of an adjustable rod inserter 190 in alternate positions during articulation of a rod, according to an embodiment herein. As shown in FIGS. 17(A) through 18(C), actuator 180 raises and lowers outer sleeve 50 and inner shafts 10, 30 together. FIGS. 17(A) through 18(C) illustrate an optional free-hand embodiment of adjustable rod inserter 1. As shown, adjustable rod inserter 190 does not require a base connector 100 to operate as a fulcrum to pivot actuator 80, as was shown in FIGS. 13(A) through 15(C). Instead, actuator 190 is free moving and allows flexible placement of adjustable rod inserter 190 during a minimally invasive surgical procedure.

In FIGS. 17(A) through 17(C), various views of adjustable rod inserter 1 in a first adjustable rod inserter position 190 are shown, where longitudinal member 130 is in a first longitudinal member position 192 and actuator 180 is in a first actuator position 194. In FIGS. 18(A) through 18(C), various views of adjustable rod inserter 1 in a second adjustable rod inserter position 200 are shown, where longitudinal member 130 is in a second longitudinal position 202 and actuator 180 is in a second actuator position 204. Second adjustable rod inserter position 200 shown in FIGS. 18(A) through 18(C) allows manipulation of longitudinal member 130 at a greater depth than first adjustable rod inserter position 190 shown in FIGS. 17(A) through 17(C). In particular, by moving actuator 180 from first actuator position 194 shown in FIG. 17(A) to second actuator position 204, shown in FIG. 18(A), longitudinal member 130 is also moved from first longitudinal member position 192 shown in FIG. 17(A) to second longitudinal member position 202 shown in FIG. 18(A).

FIG. 19, with reference to FIGS. 1(A) through 18(C), illustrates a flow diagram according to an embodiment herein. In step 210, the method of FIG. 16 describes providing an inner shaft (e.g., inner shaft 10, 30). Step 212 describes gripping a longitudinal member (e.g., longitudinal member 130) by the inner shaft (e.g., with gripping arms 12, 32 of inner shaft 10, 30). Step 214 describes mating internal threading of a rotating knob (e.g., rotating knob 70) to the shaft threading (e.g., shaft threading 20) of the inner shaft (e.g., inner shaft 10, 30). In addition, step 216 describes articulating an actuator (e.g., actuator 80 or actuator 180) operatively connected to the inner shaft (e.g., inner shaft 10, 30). Step 218 describes coupling the rotating knob to an outer sleeve (e.g., outer sleeve 50) that covers the inner shaft. Step 220 further describes rotating the rotating knob (e.g., rotating knob 70) and the outer sleeve (e.g., outer sleeve 50). Moreover, step 222 describes effectuating a linear translation by the rotation of the rotating knob (e.g., rotating knob 70) and the outer sleeve (e.g., outer sleeve 50). Step 224 describes providing a base connector (e.g., base connector 100) wrapping around the outer sleeve (e.g., outer sleeve 50). In step 226, the method of FIG. 16 describes displacing the inner shaft (e.g., inner shaft 10, 30) and the outer sleeve (e.g., outer sleeve 50) by an applied linear force to the actuator (e.g., actuator 80), the actuator pivoting from connecting arms (e.g., connecting arms 108) of the base connector (e.g., base connector 100) to translate the applied linear force to displace the inner shaft (e.g., inner shaft 10, 30) and the outer sleeve (e.g., outer sleeve 50).

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

What is claimed is:

1. An apparatus for inserting a rod, said apparatus comprising:
   an inner shaft comprising:
      a first inner shaft comprising:

a first pair of gripping arms; and
a first main body having a first length and comprising a first cross-section dimension, wherein said first main body is coupled to said first pair of gripping arms;
a second inner shaft comprising:
a second pair of gripping arms, wherein said first pair of gripping arms and said second pair of gripping arms together grip said rod; and
a second main body having said first length and comprising a second cross-section dimension, wherein said second main body is coupled to said second pair of gripping arms and said second cross-section dimension is configured to mate with said first cross-section dimension; and
a shaft threading coupled to said first main body of said first inner shaft;
a rotating knob comprising a channel bored therethrough and internal threading lining said channel, said internal threading configured to mate with said shaft threading;
an actuator comprising an actuator body and a translation cavity cut through said actuator body and an inner shaft cavity cut through said actuator body, wherein said inner shaft cavity wraps around said first cross-section dimension and said second cross-section dimension of said inner shaft;
an outer sleeve covering said first main body and said second main body of said inner shaft and coupled to said rotating knob; and
a base connector wrapping around said outer sleeve, said base connector comprising a pair of connecting arms configured to loosely mate with said translation cavity of said actuator and pivoting and translating said actuator in response to a linear force.

2. The apparatus of claim 1, further comprising a plurality of connecting hinges and pins that couple said first main body to said second main body.

3. The apparatus of claim 1, wherein said inner shaft further comprises:
a cylindrical body coupled to said shaft threading; and
a perpendicular body coupled to said cylindrical body.

4. The apparatus of claim 1, wherein a torque applied to said rotating knob and outer sleeve effectuates a linear translation in one of a first direction and a second direction.

5. The apparatus of claim 4, wherein said linear translation in said first direction translates said outer sleeve to extend and partially cover said first pair of gripping arms and said second pair of gripping arms and thereby compressing each gripping arm of said first pair of gripping arms and each gripping arm of said second pair of gripping arms together.

6. The apparatus of claim 5, wherein said linear translation in said second direction translates said outer sleeve to retract from said first pair of gripping arms and said second pair of gripping arms.

7. The apparatus of claim 1, wherein said linear force is applied in a linear direction to said actuator and effectuates a linear translation to said inner shaft and said outer sleeve in one of a first direction and a second direction.

8. The apparatus of claim 7, wherein said linear translation in said first direction and said second direction each translates said outer sleeve and said inner shaft in an opposite direction to said linear direction.

9. The apparatus of claim 7, wherein said inner shaft and said outer sleeve respond in unison to said linear translation.

10. A system for longitudinal member insertion through a percutaneous tube, said system comprising:
a longitudinal member comprising a main body and a plurality of gripping cavities;
an inner shaft comprising:
a first inner shaft comprising:
a first pair of gripping arms; and
a first main body comprising a first length and a first cross-section dimension, wherein said first main body is coupled to said first pair of gripping arms;
a second inner shaft comprising:
a second pair of gripping arms, wherein said second pair of gripping arms and said first pair of gripping arms together grip longitudinal member; and
a second main body comprising said first length and a second cross-section dimension, wherein said second main body is coupled to said second pair of gripping arms and said second cross-section dimension is configured to mate with said first cross-section dimension; and
a shaft threading coupled to said first main body of said first inner shaft;
a rotating knob with a channel bored therethrough and internal threading lining said channel, said internal threading configured to mate with said shaft threading;
an actuator comprising an actuator body and a translation cavity cut through said actuator body and an inner shaft cavity cut through said actuator body, wherein said inner shaft cavity is configured to mate with said inner shaft around said first cross-section dimension and said second cross-section dimension;
an outer sleeve covering said first main body and said second main body of said inner shaft and coupled to said rotating knob; and
a base connector wrapping around said outer sleeve, said base connector comprising a pair of connecting arms loosely mating with said translation cavity of said actuator and pivoting and translating in response to a linear force.

11. The system of claim 10, wherein said first pair of gripping arms comprise a first pair of nubs and said second pair of gripping arms comprise a second pair of nubs, and said first pair of nubs together with said second pair of nubs grip said longitudinal member at said plurality of gripping cavities.

12. The system of claim 10, further comprising a plurality of connecting hinges and pins that securely couple said first main body to said second main body.

13. The system of claim 10, wherein a torque applied to said rotating knob and outer sleeve effectuates a linear translation in one of a first direction and a second direction.

14. The system of claim 13, wherein said linear translation in said first direction translates said outer sleeve to extend and partially cover and pinch said first pair of gripping arms and said second pair of gripping arms together and thereby compress each gripping arm of said first pair of gripping arms and each gripping arm of said second pair of gripping arms together to lock said longitudinal member between said first pair of gripping arms and said second pair of gripping arms.

15. The system of claim 13, wherein said linear translation in said second direction translates said outer sleeve to retract from said first pair of gripping arms and said second pair of gripping arms and thereby unlock said longitudinal member from between said first pair of gripping arms and said second pair of gripping arms.

16. The system of claim 10, wherein said linear force is applied in a linear direction to said actuator and effectuates a linear translation to said inner shaft and said outer sleeve in one of a first direction and a second direction.

17. The system of claim 10, wherein said linear translation in said first direction and said second direction each translates said outer sleeve and said inner shaft in an opposite direction to said linear direction and thereby adjusting a depth of said longitudinal member within said percutaneous tube.

18. The system of claim 10, wherein said inner shaft further comprises a cylindrical body coupled to said shaft threading and a perpendicular body coupled to said cylindrical body.

19. The system of claim 10, wherein said outer sleeve further comprises an outer cylindrical surface and an inner polygonal surface.

* * * * *